(12) United States Patent
Cahan et al.

(10) Patent No.: US 11,142,744 B2
(45) Date of Patent: Oct. 12, 2021

(54) INFRARED SIGNAL MONITORING FOR CELL CULTURES

(71) Applicant: International Business Machines Corporation, Armonk, NY (US)

(72) Inventors: Amos Cahan, Dobbs Ferry, NY (US); Theodore G. van Kessel, Millbrook, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 140 days.

(21) Appl. No.: 15/841,786

(22) Filed: Dec. 14, 2017

(65) Prior Publication Data

US 2018/0105788 A1    Apr. 19, 2018

Related U.S. Application Data

(63) Continuation of application No. 14/965,321, filed on Dec. 10, 2015, now Pat. No. 9,879,216.

(51) Int. Cl.
    *C12M 1/34*    (2006.01)
    *C12M 1/22*    (2006.01)
    *C12M 1/36*    (2006.01)

(52) U.S. Cl.
    CPC ............ *C12M 41/46* (2013.01); *C12M 23/10* (2013.01); *C12M 41/48* (2013.01)

(58) Field of Classification Search
    CPC .................................................... C12M 41/46
    See application file for complete search history.

(56) References Cited

U.S. PATENT DOCUMENTS

| | | | |
|---|---|---|---|
| 4,889,992 A | 12/1989 | Hoberman | |
| 6,072,603 A * | 6/2000 | Parks | H04N 5/3653 348/E5.081 |
| 6,881,584 B1 | 4/2005 | Lenhard et al. | |
| 7,115,384 B2 | 10/2006 | Clark et al. | |
| 7,501,301 B2 | 3/2009 | Kovacs et al. | |
| 7,704,745 B2 | 4/2010 | Baudenbacher et al. | |
| 7,956,328 B2 * | 6/2011 | Sundaram | G01N 21/552 250/339.11 |
| 8,435,738 B2 | 5/2013 | Holmes | |
| 9,803,170 B2 | 10/2017 | Cahan et al. | |
| 2002/0098592 A1 | 7/2002 | Neilson et al. | |
| 2005/0066978 A1 * | 3/2005 | Lenhard | A61B 5/015 128/898 |
| 2005/0277186 A1 | 12/2005 | Fein et al. | |
| 2006/0140445 A1 * | 6/2006 | Cusack, Jr. | G06K 9/00261 382/103 |
| 2007/0167830 A1 | 7/2007 | Huang | |
| 2008/0106599 A1 | 5/2008 | Liu et al. | |
| 2008/0176276 A1 * | 7/2008 | Arai | C12M 41/46 435/40.5 |
| 2009/0075248 A1 | 3/2009 | Debreczeny et al. | |
| 2009/0280522 A1 | 11/2009 | Wilson | |
| 2010/0311109 A1 * | 12/2010 | Salaimeh | C12Q 1/06 435/39 |
| 2013/0177972 A1 * | 7/2013 | Green | C12M 21/08 435/288.7 |
| 2014/0380519 A1 | 12/2014 | Bangera et al. | |
| 2017/0166855 A1 | 6/2017 | Cahan et al. | |
| 2017/0166856 A1 | 6/2017 | Cahan et al. | |

FOREIGN PATENT DOCUMENTS

| | | |
|---|---|---|
| CA | 1204606 A1 | 5/1986 |
| EP | 0151855 A1 | 8/1985 |
| WO | 2012119114 A2 | 9/2012 |

OTHER PUBLICATIONS

Agema Infrared Systems "Thermovision 900 Series Users' Manual", available on Agema Infrared Systems company webpage, Publication No. 556 960, Ed. 1, copyright 1992 (Year: 1992).*
Kostelec "Basic cell counting and segmentation in Matlab", posted Apr. 24, 2014 on Ideas, Thought and Solutions webpage, available online at <<blog.pedro.si/2014/04/basic-cell-segmentation-in-matlab.html>> (Year: 2014).*
Hahn et al. "*Escherichia coli* detection using thermal images", Canadian Biosystems Engineering 48:4.7-4.13, 2006 (Year: 2006).*
Jankowski "Iterated facet model approach to background normalization." Hybrid Image and Signal Processing IV. vol. 2238. International Society for Optics and Photonics, 1994. (Year: 1994).*
List of IBM Patents or Patent Applications Treated as Related, U.S. Appl. No. 15/841,786, filed Dec. 14, 2017, 2 Pages.
Agema Infrared Systems, "Thermovision 900 Series Users' Manual", available on Agema Infrared Systems company webpage, Publication No. 556 960, ed. 1, copyright 1992.
Dickson, K. et al, "Determination of the Free-Energy Change for Repair of a DNA Phosphodiester Bond", The Journal of Biological Chemistry; May 2000, pp. 15828-15831, vol. 275, No. 21.
Lahiri, B. et al., "Detection of pathogenic gram negative bacteria using infrared thermography", Infrared Physics & Technology, Nov. 2012, pp. 485-490, vol. 55.
Selvarasu, S. et al., "Characterizing *Escherichia coli* DH5 Growth and Metabolism in a Complex Medium Using Genome-Scale Flux Analysis", Biotechnology and Bioengineering, Feb. 2009, pp. 923-934, vol. 102, No. 3.

* cited by examiner

*Primary Examiner* — Emily A Cordas
(74) *Attorney, Agent, or Firm* — Cantor Colburn LLP; Kristofer Haggerty

(57) ABSTRACT

The present invention is directed to an apparatus for monitoring a cell culture comprising a) one or more infrared sensors positioned adjacent to a cell culture, the one or more infrared sensors capable of recording an infrared heat signal from the cell culture; b) a power source in electrical communication with the one or more infrared sensors; c) a data storage and computation device configured to receive and analyze the infrared heat signal from the one or more infrared sensors; and d) a transmitter device in electrical communication with the storage and computation device; wherein the apparatus monitors the pattern of heat production in the cell culture. The present invention is also directed to methods for monitoring and analyzing the metabolic activity of cells using the above apparatus.

7 Claims, 5 Drawing Sheets

INFRARED SIGNAL MONITORING FOR CELL CULTURES

This application is a continuation of U.S. application Ser. No. 14/965,321, titled "INFRARED SIGNAL MONITORING FOR CELL CULTURES" filed Dec. 10, 2015, the contents of which are incorporated by reference herein in its entirety.

BACKGROUND

The present invention relates to a system for monitoring of cell cultures, and in particular to a system of monitoring cell cultures using infrared sensors and cameras to detect changes in the pattern of heat production within metabolically active cells.

Cells are commonly grown in the lab on dishes or in wells that contain nutrients. These may be human or animal cells, as well as microorganisms such as bacteria, fungi and archaea used in research or clinical diagnostics and therapeutics. Cells are typically grown in an incubator with controlled temperature and humidity. To determine the degree of growth of cells, they are most often monitored visually by a human. For example, samples from potential infection sites in patients are inoculated on a Petri dish and a lab technician may visually inspect the dish after a few hours to a few days to spot signs of bacterial colony formation. This is labor intensive and also is associated with a risk for contamination. When cells require a strict anaerobic environment, visually inspecting them entails exposing them (even if for a limited period of time) to air, which may delay their growth or lead to their death. Visual inspection is widely used to determine bacterial susceptibility to antibiotics, for example using the disc-diffusion test, wherein bacterial growth is inhibited around a disc containing an antibiotic drug. However, it is practically impossible for humans to continuously monitor cells in culture. Moreover, for microorganism growth to be visually evident to the naked eye takes an extremely high number of cells to be accumulated.

Yet the ability to continuously monitor cells in culture is desirable. For example, it could shorten the time until an infection is diagnosed or the time needed to determine what the most effective antibiotic would be to treat a patient. Moreover, cells may stop growing or die due to lack of nutrients, unbalanced ambient conditions or infection by viruses, phages and fungi. Early detection of impaired cell growth is important in addressing the problem causing impaired growth. For example, early detection may allow for ambient conditions to be modified before cells experience irreversible damage. Early detection of an infection affecting cells may allow for control measures to be taken to prevent spread of the infection to other cells or specimens.

Continuous monitoring of the rate of cell growth may also be used to support research related to the use of medications. When medications or other interventions such as genetic modifications intended or potentially capable of cell growth or metabolism are investigated, continuous monitoring can quantify their effect on cells and provide a measure of the kinetics of their action. Impairment in cell growth or metabolic activity, or increased rate of cell growth may be adverse effects of drugs. Continuous monitoring of cell growth may allow for better detecting such effects.

With the advent of technology, cells are often cultured in small compartments such as wells, which are more difficult to visually inspect. Spectrometry is used to measure cell concentration in a liquid medium but this requires manually positioning of wells or other containers in a designated device which is not located within the incubator. This is labor intensive, increases the risk of mistakes and requires displacement of cells from their preferred culture environment, which may have adverse effects on cell growth. Automated agar plate inoculation systems exist that perform seeding of microbiologic samples on plates and monitor their growth using a camera but these do not use infrared cameras, and are not commonly used in the research setting due to their inflexibility and high price.

SUMMARY

In one embodiment, the present invention is directed to an apparatus for monitoring a cell culture comprising a) one or more infrared sensors positioned adjacent to a cell culture, the one or more infrared sensors capable of recording an infrared heat signal from the cell culture; b) a power source in electrical communication with the one or more infrared sensors; c) a data storage and computation device configured to receive and analyze the infrared heat signal from the one or more infrared sensors; and d) a transmitter device in electrical communication with the storage and computation device; wherein the apparatus monitors the pattern of heat production in the cell culture.

In another embodiment, the present invention is directed to a method for monitoring and analyzing the metabolic activity of cells comprising the steps of: a) recording high definition images of infrared spectrum emission from the cells and from a reference sample using the above-described apparatus; b) analyzing the images by computerized image recognition to determine at least the amount of heat produced by the cells, the regions of the culture where the heat is produced, and the change in heat production over time to provide an uncorrected analysis; and c) optionally correcting the analysis by comparing the images of the cells with the images of the reference sample to provide a corrected analysis.

These and other embodiments will become apparent from the following detailed description of the invention.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

There is a need for automated, low cost means to monitor cell growth to save time, reduce labor associated with lab work, save money lost due to waste of reagents and equipment, and shorten time to microbiologic results that may affect patient treatment and outcomes.

The present invention relates to an apparatus and method for infrared monitoring of cell cultures, and more specifically to an apparatus and method that utilizes infrared sensors or cameras to detect changes in the pattern of heat production within metabolically active cells. The present invention offers the advantages of automation, ease of use, low cost, and speed of data acquisition that could improve cell culture growth conditions, patient treatment, and outcomes.

Figure 1:
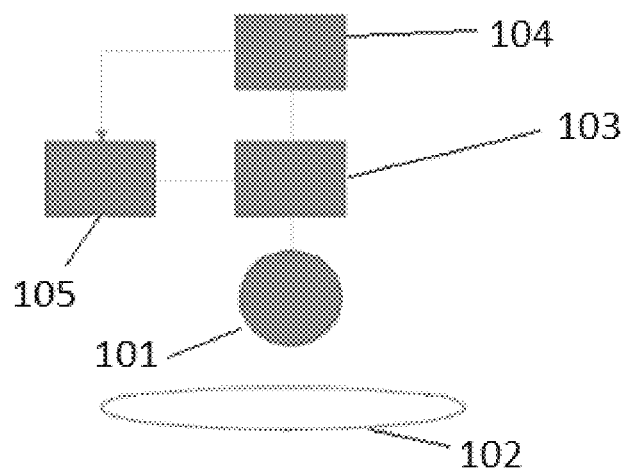
FIG. 1 illustrates one embodiment of the cell growth monitoring system of the invention.

As indicated above and shown in FIG. 1, the present invention is directed to an apparatus for monitoring the pattern of heat production in a cell culture. The apparatus comprises (a) one or more infrared sensors 101 positioned adjacent to a cell culture 102; (b) a power source 103 in electrical communication with the infrared sensors 101; (c) a data storage and computation device 104 configured to receive and analyze the infrared heat signal from the sensors; and (d) a transmitter device 105 in electrical communication with the storage and computation device 104. Each of these components is described in more detail below.

The apparatus of the present invention includes one or more infrared (IR) sensors. The infrared sensors used in the apparatus of the invention may be any sensor that effectively senses infrared radiation (e.g. radiation from 700 nm-1 mm). Examples of useful sensors that may be implemented in the apparatus of the invention include, but are not limited to, cameras, bolometers, semiconductors, and the like. In one preferred embodiment, the IR sensor is a camera, such as a camera in the conventional sense, with a transparent viewing port, and can incorporate lenses or other means for focusing incoming radiation. In one embodiment, the IR sensors can be cameras which record high definition images, wherein high definition can be defined as being on the order of 80×60 pixels or more. The IR sensors can include bolometers, which measure the power of incident radiation by the measuring the heating of a material with temperature-dependent electrical properties. The IR sensors can include semiconductors sensitive to IR light. The IR sensors can be sensitive to many wavelengths of IR radiation, such as far IR (e.g. radiation from 15000 nm-1 mm), near IR (e.g. radiation from 700-3000 nm), or any wavelength band in between.

The IR sensors of the invention are preferably passive IR sensors, defined as sensors that measure IR light radiating from objects, wherein the sensor itself does not radiate energy at the sample for detection purposes. A passive IR sensor detects changes in the amount of IR radiation impinging upon it, which varies depending on the temperature and surface characteristics of the objects in front of the sensor. The sensor converts the resulting change in incoming IR radiation into a change in output value which can be used to detect and record the IR radiation.

The cell culture can be contained in a culture vessel. In one embodiment, the culture vessel can be a container such as a petri dish, test tube, flask, and the like. In other embodiments, the culture vessel can be a well, which can be part of a multi well plate, or can be the well plate itself. The culture vessel can be sealed, closed with a lid, or open to the environment on at least one surface. In some embodiments, the culture vessel is open on the top, such as an open well with no lid. In other embodiments, the culture vessel is closed but has one or more access ports allowing inflow or outflow of material, including liquids, solids, gases, suspensions, and the like.

The IR sensors can be placed adjacent to the sample which can be cell culture, medium, or reference sample, and which can be contained in a culture vessel. As defined herein, "adjacent" means any orientation that is sufficiently close and properly situated to detect IR radiation emitted from the sample. For example, the sensor can be placed above, underneath, or on any side of the sample. In one embodiment, the sensor is placed above the sample, wherein the sample is a cell culture. In another embodiment, the sensor can be placed directly on the outer surface of a culture vessel containing the sample. In another embodiment, the sensor is placed a short distance away from the sample, for example less than 100 cm, less than 50 cm, or less than 30 cm. In some embodiments, the IR sensor can be placed on the lid of the culture vessel, such as a petri dish, or replace the lid of the culture vessel. In some embodiments, the sensor can be placed inside the culture vessel, and is optionally immersed in the medium containing the sample.

IR radiation from the culture vessel can be detected by a single IR sensor, or by an array of IR sensors, for example 2, 3, 4, 5, 6, or more IR sensors. The array of IR sensors or a single IR sensor can be arranged to detect IR radiation from different regions of the cell culture. The culture vessel must have a structure, or at least a portion of its structure, that is transparent to IR radiation so that the IR sensors can detect IR emissions through the wall of the culture vessel, unless the IR sensors are located inside the culture vessel. "Transparent to IR" is defined here as a material that permits nearly 100%, at least 95% or at least 90% transmission of infrared radiation. For example, the culture vessel may have at least a portion of its structure made of IR transparent material such as chalcogenide glass, IR grade fused silica, sapphire, calcium fluoride, silicone, zinc sulphite, cadmium telluride, quartz, IR transparent plastics, and the like.

The apparatus according to the present invention includes a power source in electrical communication with the IR sensors. Power sources suitable for implementation in the apparatus and methods of the invention can be of a kind that store power, such as batteries or capacitors, or receive power without wires, such as by solar power or inductive coupling. In some embodiments the power source receives power through a wired connection with an electrical main, external battery, external generator, or the like. In some embodiments, the power source can be in electrical communication with an amplifier, a data storage and computation device, a transmitter, or a control unit. In some embodiments, a single power source supplies power to all the components of the apparatus which require power. In other embodiments, there can be multiple power sources, such that some power sources supply some components and other power sources supply other components.

A data storage and computation device is in communication with the sensor and/or amplifier, and is configured to receive and analyze the IR signal. The data storage and computation device can be a standard digital computer, or simply a printed circuit board and memory device, or other devices that accomplish the same function. The data storage and computation device can also be in communication with a power supply, a transmitter, and a control unit. The data storage and computation device can analyze the data in the IR signal to generate an analyzed signal or further analyze to produce image data which can be viewed or sent to other devices.

Figure 2:
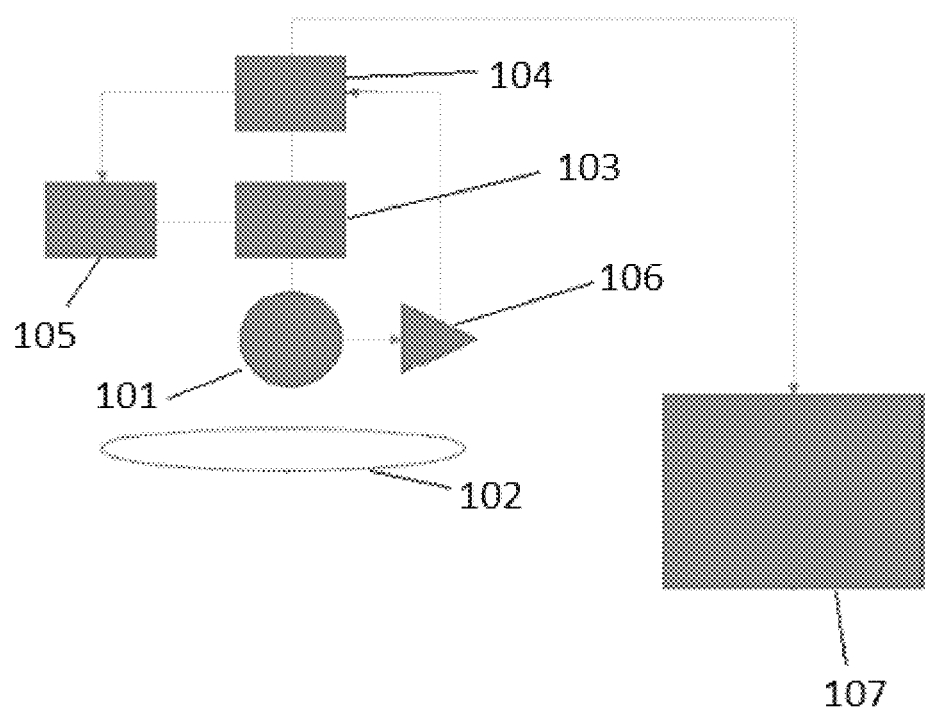
FIG. 2 illustrates another embodiment of the cell growth monitoring system of the invention including an amplifier and a control unit.

In some embodiments a transmitter can be in communication with the sensor, amplifier, data storage and communication device, control unit, and/or power source. As shown in FIG. 2, in one embodiment, the transmitter 105 receives information from the data storage and computation device 104 and transmits the information to a control unit 107. The control unit 107 can exchange information from the computation device 104 via wired connection e.g. ethernet, or alternately through the transmitter-receiver 105. The transmitter can send the information via a wired connection or by wireless transmission. The wireless transmission can be by technology such as BLUETOOTH (short link radio technology), WiFi, RFID, or the like.

As shown in FIG. 2, the apparatus includes an amplifier 106 in communication with the IR sensor 101. The amplifier 106 can amplify the signal received by the IR sensor 101. The amplifier 106 can be incorporated with the sensor component or external to the sensor 101. In some embodiments, the amplifier 106 is positioned between the IR sensor 101 and the data storage and computation device 104.

As shown in FIG. 2, a control unit 107 receives information from other components of the system. The control unit 107 can be any computation device known in the art such as a smartphone, laptop, or cloud service. The control unit 107 can receive IR signal information, and can analyze and process it to produce a determination of heat production in the cell culture. In some embodiments, the control unit 107 is in communication with the data storage and computation device 104. In some embodiments, the control unit 107 produces an analysis of metabolic activity of the cell culture over time. In some embodiments, the functions of transmitter 105 and data storage and computation device 104 are incorporated in the control unit 107; the control unit 107 in such an embodiment receives data from the IR sensors 101, analyzes it, and then processes it to produce a determination of heat production in the cell culture.

In some embodiments of the apparatus of the invention, the control unit can receive information other than IR heat signal. Such as information can include pH, humidity, and carbon dioxide concentration, or other parameters related to cellular growth. This information can come from sensors in addition to the IR sensors, for example pH sensors to detect pH.

In some embodiments the control unit can modify the growth conditions of the cell culture as desired by the user. For example, if the control unit finds the growth of the cells is too slow, the control unit can adjust the temperature of the cell culture, and if the pH of the cell culture is out of the desired range, the control unit can adjust the $CO_2$ concentration.

Figure 3:
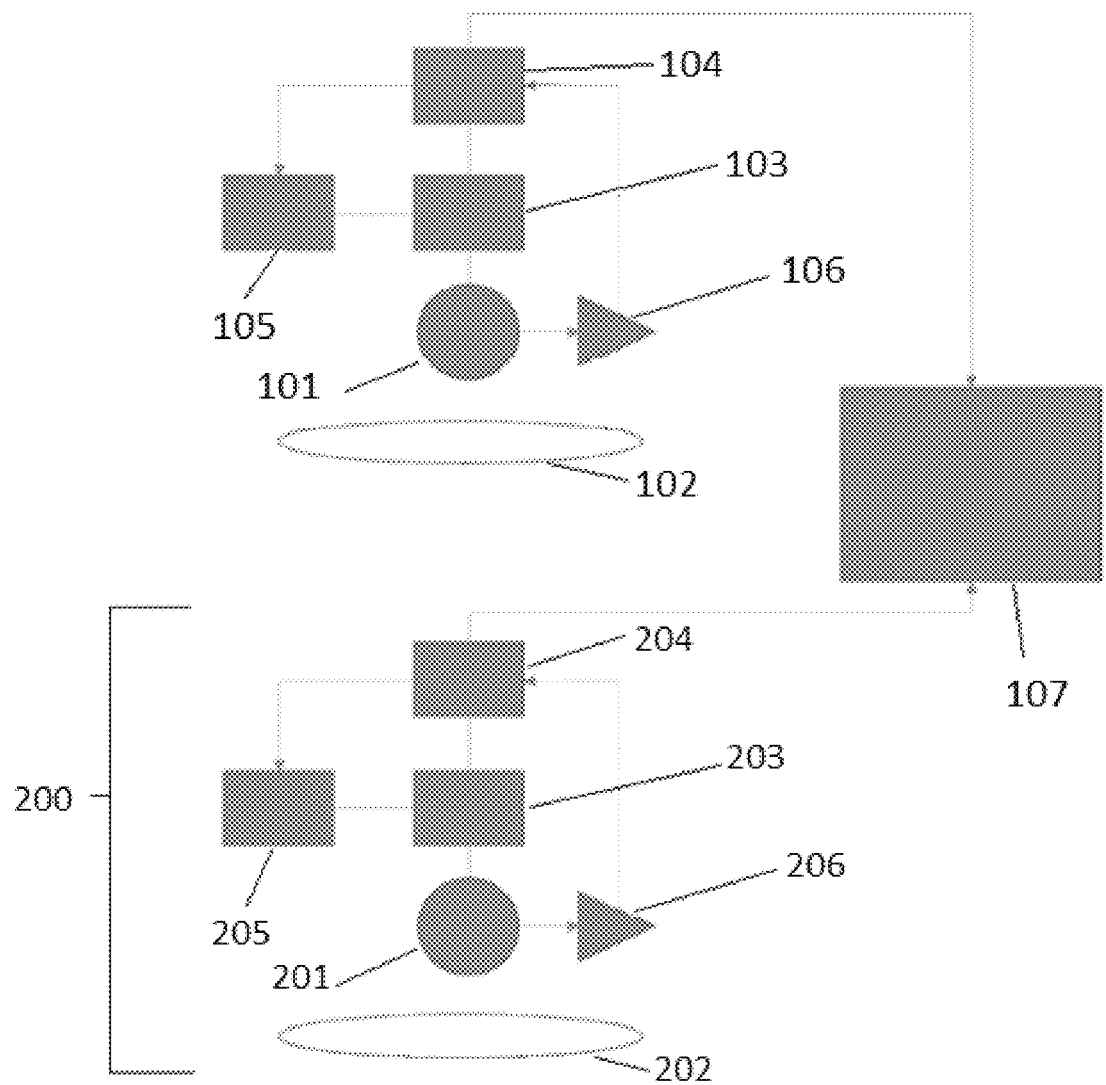
FIG. 3 illustrates another embodiment of the cell growth monitoring system of the invention including a reference component.

In some applications of the apparatus and method of the invention, it may be desirable to compare the infrared signal from the cell culture to a reference sample. As shown in FIG. 3, the apparatus of the present invention may therefore also include embodiments which include a reference component 200 with one or more reference samples 202. In addition to one or more reference samples, the reference component is in communication with the control unit, includes one or more IR sensors, and can include an amplifier 206, transmitter, digital computer, and power source configured similarly to the components used to monitor the cell culture. In one embodiment the system comprises one or more reference infrared sensors 201 positioned adjacent to a reference sample 202; a reference power source 203 in electrical communication with the reference infrared sensors 201; a reference data storage and computation device 204 configured to receive and analyze the infrared heat signal from the reference infrared sensors 201; a reference transmitter device 205 in electrical communication with the reference storage and computation device 204 and configured to transmit information to a control unit 107.

The reference samples can contain only media in a culture vessel, or can contain both cells and media. The reference component allows comparison of the pattern of heat production in the cell culture with the pattern of heat production in the reference sample. This comparison can be used to reduce signal noise or to correct the IR signal from the non-reference cell culture. In some embodiments, the reference sample includes cells different from the cell culture sample and is used to compare the heat production of different cell types. In other embodiments the reference sample contains cells similar to those in the cell culture, but grown under different conditions.

Figure 4:
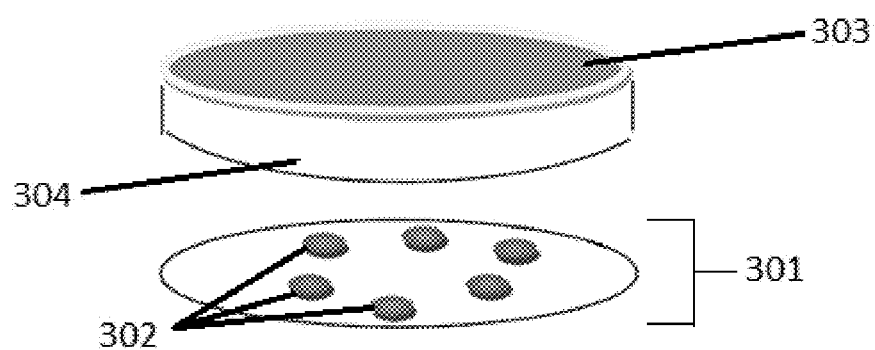
FIG. 4 illustrates another embodiment of a cell growth monitoring of the invention including a sensor array.

As shown in FIG. 4, in some embodiments of the invention one or more IR sensors may comprise a sensor array 301. In this embodiment, the sensor array 301 comprises multiple individual IR sensors 302 which are used to monitor heat production caused by metabolism and growth of a cell culture 303 in a petri dish 304.

Sensor array 301 can comprise 2, 3, 4, 5, 6, or more individual sensors 302. The sensors in the sensor array can be arranged in any suitable pattern which allows measurement of the desired regions of the cell culture. In some embodiments, parts of the sensor array measure IR signal from the portion of the cell culture with cells, and portions of the sensor array measure IR signal from a portion of the cell culture without cells.

Figure 5:
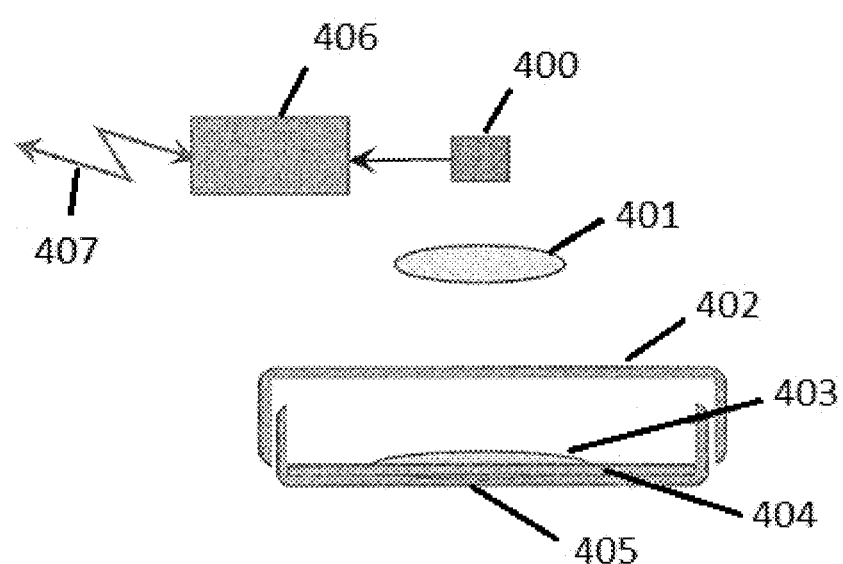
FIG. 5 illustrates an infrared system for cell culture monitoring including an infrared lens in accordance with the present invention.

As shown in FIG. 5, in one preferred embodiment of the invention an infrared camera is used to monitor the growth of a cell culture. A cell culture 403 creates heat as it grows on a growth medium 404 in a culture dish 405, wherein culture dish 405 is covered on its top surface by an infrared transparent lid 402. The creation of heat by cell culture 403 results in infrared emission from the cell culture that is greater than the surrounding culture dish 405, medium 404 and lid 402. An infrared camera 400 is positioned adjacent to lid 402, with a lens 401 interposed between camera 400 and lid 402. Infrared camera 400 is in electrical communication with computer 406 which has a network connection 407. In one embodiment, one or more lenses 401 are positioned between the IR camera 400 and cell culture 403.

An infrared transparent lid 402 is preferably chosen with low emissivity to allow the infrared emission from the culture to be visible to the infrared camera 400. In some embodiments the entire lid 402 is IR transparent. In other embodiments, a portion of the lid 402 is IR transparent to form an IR window, and the IR camera 400 is situated to detect IR emission that passes from the cell culture 403 through the IR window. The lens 401 is preferably chosen so that it is transparent to and can focus IR radiation. Such a lens may be termed an IR lens. In one embodiment the lid of the culture vessel comprises an IR transparent material configured to function as a lens.

In some embodiments of the invention the cell culture is grown in an enclosure such as an incubator. In such embodiments, all the components of the apparatus can be entirely outside the incubator (for example, the IR sensor can detect IR from the cell culture through a window or other IR transparent surface of the incubator), or some components can be inside the incubator and some outside. For example, in an embodiment the computer, control unit, and power source can be outside the incubator and the transmitter, IR sensor, and amplifier are inside the incubator.

The cell culture that may be monitored using the apparatus and method of the invention may be one or more cells in a growth medium, the cells of a kind that emits IR radiation when metabolically active. The cells can be eukaryotic, prokaryotic, or archaea. If eukaryotic, the cells can be from a one celled or multicellular organism. If eukaryotic, the cells can be connected to each other as part of a tissue, and can be a complete organism including an embryo. In some embodiments, the cells can be an embryo generated as part of an in vitro fertilization (IVF) procedure.

The cells can be grown in any medium known in the art, for example a medium which is solid or semisolid, such as agar. For a solid or semisolid medium, the cells can be grown on the surface of the medium or in the interior of the medium. In some embodiments the cells can be grown in a liquid medium, such as a liquid nutrient broth.

In another embodiment of the invention, the apparatus may be implemented in a method for monitoring and analyzing the metabolic activity of cells comprising the steps of: a) recording high definition images of infrared spectrum emission from the cells and from a reference sample using the apparatus of the invention; b) analyzing the images by computerized image recognition to determine at least the amount of heat produced by the cells, the regions of the culture where the heat is produced, and the change in heat production over time to provide an analysis; and c) optionally correcting the analysis by comparing the images of the cells with the images of the reference sample to provide a corrected analysis.

In one embodiment of the method of the invention, the recording step comprises detecting the IR light with an IR sensor to produce a high definition IR image on the sensor, and converting the high definition infrared image on the sensor to a digital image that is relayed directly or indirectly to a computing device, and may be printed, scanned, or displayed to produce a form of recording visible to a user.

In one embodiment of the method of the invention, analyzing the images comprises windowing (sub-section) of the image and interpreting the image relative to previous images to detect whether culture growth is proceeding as intended. A variety of image processing methods can be used to evaluate the infrared images that will be recognized by those skilled in the art as well as automatically by image recognition technology used by computerized systems trained for this purpose. The raw infrared image is preferably first processed using signal gain and offsets and lookup table balancing to give high contrast to the desired culture features in the image. In some embodiments the images of infrared spectrum emission are coupled with other signals to interpret the infrared emission pattern or to augment or verify interferences from the infrared pattern. The other signals can include signals such as gas analysis, spectroscopy, colorimetry, visible or ultraviolet light, and the like.

In some embodiments, the analyzing step can further comprise determining the approximate size of the culture by counting the number of now high contrast elements in the image (blob finding). Culture sizes can be compared to results in previous images taken over time to determine the rate of growth of the sample. In other embodiments, sequential filtered images may be subtracted from previous images and the resultant pixels counted to determine the differential growth. Those skilled in the art will recognize that a wide variety of methods similar to those outlined above can be used to determine the change in culture size.

Analysis of IR images can allow for identification of locations in which heat is produced by metabolically active cells and monitoring this heat production over time. In some embodiments this allows for the detection of early stage bacterial growth, estimation of the inoculum, predicting the type of microorganism(s) growing by the spatial pattern of growth and the growth rate, identification of metabolic responses to interventions (such as exposing cells to a drug, change in nutrients provided or manipulating gene expression), as well as early detection of malfunction of cells due to a disease (e.g., viral infection of cells) or in plausible ambient conditions. The apparatus and method of the present invention can potentially add to the ability to differentiate healthy from sick tissues sampled from a human or animal body. The present invention can allow faster evaluation of cell growth than is possible by simple visual inspection. Other methods of determining cell metabolism and growth involve measurement of gas such as $CO_2$ produced by living cells, but these methods would not work for unsealed containers such as petri dishes, whereas the apparatus and method of the present invention can work in a sealed or unsealed environment.

In some embodiments the apparatus is used to detect cell growth and determine the rate of cell growth or cell metabolism. In other embodiments the apparatus is used to estimate the initial inoculum or microorganism taxa. In other embodiments the apparatus is used to evaluate cell response to a drug. Cell response to a drug can be measured by the implanting of drug-infused discs in the cell culture, and subsequent measurement of the reduction in rate or extent of growth or metabolism. In some embodiments the evaluation of cell response to a drug measures antibiotic susceptibility.

In another embodiment, the analyzing step comprises processing to increase contrast between cells and medium to create higher contrast elements corresponding to the cells in the image; and then counting the higher contrast elements in the image to provide an estimate of the metabolic activity of the cells; and then comparing metabolic activity over time to determine the rate of growth of the cells.

According to one embodiment of the invention, an apparatus for monitoring a cell culture comprises a) one or more infrared sensors positioned adjacent to a cell culture, said one or more infrared sensors capable of recording an infrared heat signal from said cell culture; b) a power source in electrical communication with said one or more infrared sensors; c) a data storage and computation device configured to receive and analyze said infrared heat signal from said one or more infrared sensors; and d) a transmitter device in electrical communication with said storage and computation device; wherein said apparatus monitors the pattern of heat production in said cell culture.

In another embodiment, said one or more infrared sensors comprise one or more infrared cameras.

In another embodiment, the apparatus further comprises an amplifier positioned between said one or more infrared sensors and said data storage and computation device.

In another embodiment, the apparatus further comprises a control unit in communication with said data storage and computation device.

In another embodiment, the apparatus further comprises a reference component in communication with said control unit, said reference component comprising a) one or more infrared sensors positioned adjacent to a reference sample, said one or more infrared sensors capable of recording an infrared heat signal from said reference sample; b) a power source in electrical communication with said one or more infrared sensors; c) a data storage and computation device configured to receive and analyze said infrared heat signal from said one or more infrared sensors; and d) a transmitter device in electrical communication with said storage and computation device; wherein said reference component monitors the pattern of heat production in said reference sample and wherein said control unit compares said pattern of heat production in said cell culture with said pattern of heat production in said reference sample.

In another embodiment, said cell culture is contained in a culture vessel.

In another embodiment, said culture vessel is a petri dish.

In another embodiment, said culture vessel is a flask.

In another embodiment, said culture vessel is a test tube.

In another embodiment, said culture vessel is a well plate.

In another embodiment, said culture vessel comprises infrared transparent materials.

In another embodiment, said one or more infrared sensors are positioned above said cell culture.

In another embodiment, the apparatus further comprises one or more lenses positioned between said one or more infrared sensors and said cell culture.

In another embodiment, the infrared sensors are located on the outer surface of the culture vessels.

In another embodiment, the infrared sensors are located on the lids or replacing the lids of the culture vessels.

In another embodiment, the apparatus further comprises a component for wired or wireless data transmission to a remote computer, handheld device, or cloud.

In another embodiment, the infrared sensors can record continuously or intermittently.

In another embodiment, the infrared sensors can be sterilized using techniques that do not damage said sensors.

In another embodiment, the infrared sensors and cell cultures are both located in a cell culture incubator.

In another embodiment, the control unit can receive information other than heat signal, wherein said information other than heat signal can include pH, humidity, and carbon dioxide concentration.

In another embodiment, the control unit can modify the growth conditions of the cell culture.

In another embodiment, the images of infrared spectrum emission are used to detect cell growth.

In another embodiment, the images of infrared spectrum emission are used to monitor the effect of a drug.

In another embodiment, the images of infrared spectrum emission are used to detect antibiotic susceptibility.

In another embodiment, the images of infrared spectrum emission are used to estimate the initial inoculum or microorganism taxa.

In another embodiment, the images of infrared spectrum emission are coupled with other signals to interpret the infrared emission pattern or to augment or verify interferences from the infrared pattern; wherein the other signals can comprise gas analysis, spectroscopy, colorimetry, or visible or ultraviolet light.

In another embodiment, the cells are eukaryotic, prokaryotic, or archaea.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for monitoring and analyzing metabolic activity of a cell culture, the method comprising the steps of:

recording first high definition images of infrared spectrum emission from the cell culture over time in a medium and second high definition images of infrared spectrum emission from a reference sample using high definition infrared sensors, the reference sample comprising a second cell culture having at least one of a different cell type or a same cell type grown under different conditions, the cell culture in a culture vessel, the high definition infrared sensors comprising a lid of the culture vessel configured as an infrared lens;

analyzing the first high definition images by computerized image recognition to determine at least an amount of heat produced by the cell culture, two or more different regions of the cell culture where heat is produced, and a change in heat production in the two or more different regions over time to provide an analysis, wherein the two or more different regions include a first region of the cell culture having cells and a second region of the cell culture without cells;

correcting the analysis by comparing the first high definition images of infrared spectrum emission of the cells with the second high definition images of infrared spectrum emission of the reference sample to provide a corrected analysis comprising reduced signal noise;

providing a metabolism analysis based upon the corrected analysis, wherein the metabolism analysis comprises determining a change in metabolism based upon the change in heat production, wherein an increase in heat production is correlated with an increase in metabolism and a decrease in heat production is correlated with a decrease in metabolism;

processing the first high definition images to increase contrast between cells and the medium to create higher contrast elements corresponding to the cells in the images;

windowing a first image of the first high definition images;

windowing a second image of the first high definition images, wherein the second image is a previous image relative to the first image;

counting the higher contrast elements in the images to determine a size of the cell culture;

comparing a number of high contrast elements in the first image to a number of high contrast elements in the second image to determine a rate of growth of the cell culture based on a change in culture size over time; and modifying a growth condition of the cells in response to the rate of growth of the cell culture falling outside of a desired range, wherein modifying the growth condition comprises at least one of adjusting a temperature of the cell culture and adjusting a $CO_2$ concentration of the cell culture to increase or decrease the rate of growth.

2. The method of claim 1, comprising monitoring the effect of a drug.

3. The method of claim 1, comprising detecting antibiotic susceptibility.

4. The method of claim 1, comprising estimating the initial inoculum or microorganism taxa.

5. A method for monitoring and analyzing metabolic activity of cells in a cell culture comprising the steps of:
  recording first high definition images of infrared spectrum emission from the cell culture over time in a medium and second high definition images of infrared spectrum emission from a reference sample using high definition infrared sensors, the reference sample comprising a second cell culture having at least one of a different cell type or a same cell type grown under different conditions the cell culture in a culture vessel, the high definition infrared sensors comprising a lid of the culture vessel configured as an infrared lens;
  analyzing the first high definition images by computerized image recognition to determine at least an amount of heat produced by the cell culture, two or more different regions of the cell culture where heat is produced, and a change in heat production in the two or more different regions over time to provide an analysis, wherein the two or more different regions include a first region of the cell culture having cells and a second region of the cell culture without cells;
  providing a metabolism analysis based upon the analysis, wherein the metabolism analysis comprises a determination of a change in metabolism based upon the change in heat production, wherein an increase in heat production is correlated with an increase in metabolism and a decrease in heat production is correlated with a decrease in metabolism processing the first high definition images to increase contrast between cells and the medium to create higher contrast elements corresponding to the cells in the images;
  windowing a first image of the first high definition images;
  windowing a second image of the first high definition images, wherein the second image is a previous image relative to the first image counting the higher contrast elements in the images to determine a size of the cell culture;
  comparing a number of high contrast elements in the first image to a number of high contrast elements in the second image to determine a rate of growth of the cell culture based on a change in culture size over time; and
  modifying a growth condition of the cells in response to the rate of growth of the cell culture falling outside of a desired range, wherein modifying the growth condition comprises at least one of adjusting a temperature of the cell culture and adjusting a $CO_2$ concentration of the cell culture to increase or decrease the rate of growth.

6. The method of claim 5, further comprising coupling each of the first image and the second image with a signal selected from the group consisting of a gas analysis signal, a spectroscopy signal, a colorimetry signal, a visible light signal, and a ultraviolet light signal to interpret the infrared emission pattern or to augment or verify interferences from the infrared pattern.

7. The method according to claim 5, wherein analyzing the first high definition images comprises processing the first high definition images with signal gain, offsets, and look up table balancing to create high contrast image features.

* * * * *